United States Patent
Font Caselles

(10) Patent No.: US 11,298,278 B2
(45) Date of Patent: Apr. 12, 2022

(54) HYGIENE PRODUCT FOR PERSONAL USE

(71) Applicant: Ramón Vendrell Vila, Barcelona (ES)

(72) Inventor: Ramón Font Caselles, Barcelona (ES)

(73) Assignee: Ramón Vendrell Vila, Barcelona (ES)

( * ) Notice: Subject to any disclaimer, the term of this patent is extended or adjusted under 35 U.S.C. 154(b) by 566 days.

(21) Appl. No.: 16/321,177

(22) PCT Filed: Jul. 26, 2017

(86) PCT No.: PCT/ES2017/000094
§ 371 (c)(1),
(2) Date: Jan. 28, 2019

(87) PCT Pub. No.: WO2018/020061
PCT Pub. Date: Feb. 1, 2018

(65) Prior Publication Data
US 2020/0060901 A1  Feb. 27, 2020

(30) Foreign Application Priority Data

Jul. 28, 2016 (ES) .............................. ES210600532U

(51) Int. Cl.
*A61F 13/51* (2006.01)
*A61F 13/53* (2006.01)
(Continued)

(52) U.S. Cl.
CPC ........ *A61F 13/8405* (2013.01); *A61F 13/513* (2013.01); *A61F 13/51401* (2013.01);
(Continued)

(58) Field of Classification Search
CPC ............ A61F 13/51113; A61F 13/8405; A61F 2013/51117; A61F 2013/8455;
(Continued)

(56) References Cited

U.S. PATENT DOCUMENTS 3,490,454 A * 1/1970 Goldfarb ................. A61L 15/44
604/359
3,585,998 A * 6/1971 Hayford ............. A61F 13/8405
604/360

(Continued)

*Primary Examiner* — Catharine L Anderson
(74) *Attorney, Agent, or Firm* — Maier & Maier, PLLC

(57) ABSTRACT

The invention relates to a hygiene product for personal use, which comprises at least an impermeable breathable outer first layer (11), a liquid-absorbing second layer (12) and a third layer (13) of non-woven fabric intended to be in contact with the skin of the user. The hygiene product can be a sanitary towel, dressing, tampon, absorbent nappy, nursing pad or similar product or use. The absorbent second layer (12) comprises a hydrophilic cotton core formed by separated fibers facing or oriented in all directions. The absorbent second layer (12) and/or cotton non-woven third layer (13) of the product preferably incorporate a plurality of microcapsules (3) containing active ingredients (32) for treating the skin, said ingredients being encapsulated in an outer cover (31) of biocompatible material that degrades during the use of the hygiene product and releases the active ingredients (32) during the use of the hygiene product (1).

5 Claims, 1 Drawing Sheet

(51) Int. Cl.
*A61F 13/84* (2006.01)
*A61F 13/513* (2006.01)
*A61F 13/514* (2006.01)
*A61F 13/531* (2006.01)
*A61F 13/56* (2006.01)

(52) U.S. Cl.
CPC ........ *A61F 13/531* (2013.01); *A61F 13/5611* (2013.01); *A61F 2013/53035* (2013.01)

(58) Field of Classification Search
CPC ...... A61F 2013/8458; A61F 2013/8461; A61F 2013/8464
See application file for complete search history.

(56) References Cited

U.S. PATENT DOCUMENTS

| | | | | |
|---|---|---|---|---|
| 5,951,534 | A * | 9/1999 | Cummings | A61F 13/8405 604/359 |
| 2012/0323200 | A1* | 12/2012 | Gagliardini | A61L 15/20 604/372 |
| 2014/0257228 | A1* | 9/2014 | Wang | A61F 13/505 604/385.14 |
| 2014/0377207 | A1* | 12/2014 | Scavone | A61L 15/20 424/76.5 |
| 2018/0333515 | A1* | 11/2018 | Rezai | A61L 15/46 |

* cited by examiner

HYGIENE PRODUCT FOR PERSONAL USE

OBJECT OF THE INVENTION

The present invention comprises at least an impermeable breathable first layer, a liquid-absorbing second layer and a third layer of non-woven fabric intended to be in contact with the skin of the user.

This hygiene product has a series of characteristics intended to make it possible to release active products with cosmetic or medicinal properties when it remains in contact with the skin of the user, and to distribute the liquids absorbed along the entirety of the volume of the absorbent intermediate second layer.

FIELD OF APPLICATION OF THE INVENTION

This invention is applicable in the manufacture of disposable hygiene products for personal use, such as: sanitary towels, dressings, tampons, incontinence nappies, nursing pads or any other product intended to be in direct contact with the skin.

BACKGROUND OF THE INVENTION

There are currently in the market numerous disposable, or non-reusable, hygiene products for personal use, such as sanitary towels, dressings, tampons, incontinence nappies or nursing pads as mentioned above, which have the aim of absorbing and retaining liquids released by the organism, such as menstrual discharge, urine, or breast milk.

The hygiene products currently used to absorb and retain these liquids usually comprise: an impermeable layer, an absorbent layer, and a layer of non-woven fabric intended to remain in contact with the skin of the user, which allows the passage of liquids to the absorbent layer.

The impermeable layer acts as a containment barrier preventing the liquids entering the absorbent core from coming out, preventing the clothes of the user from getting stained.

These hygiene products have a very specific use limited to the aforementioned absorption and retention of bodily fluids, and they also have the drawback that the liquids released by the body of the user access a certain area of the absorbent layer and are not distributed along the entirety of the constituent material, which makes a limited use of the absorption capacity of the hygiene product.

Since often the people that use these hygiene products experience different problems, such as irritation, risk of infection, dryness, etc., in the area where said hygiene products are applied on, the technical problem addressed is the development of a hygiene product for personal use that makes it possible to use optimally the absorption capacity of the absorbent layer located between the impermeable layer and the cotton non-woven layer, and simultaneously, use said hygiene product as a support for a suitable active product in order to apply in said area a suitable cosmetic or medical treatment for the common ailments experienced in said areas, without requiring the user to carry out any specific action nor to apply the product of the treatment.

DESCRIPTION OF THE INVENTION

The hygiene product for personal use that is the object of the invention, which can be a sanitary towel, tampon, absorbent nappy, nursing pad or similar, comprises at least: an impermeable, breathable first layer; a liquid-absorbing second layer and a third layer of non-woven fabric intended to be in contact with the skin of the user; it has a series of characteristics that make it possible to address the aforementioned problem, both in that it incorporates an active product for treating the skin in the area that is in contact with the hygiene product, as well as in that it makes optimal use of the liquid absorption capacity of the layer of absorbent material.

In order to do so and according to the invention, the absorbent second layer comprises a hydrophilic cotton core formed by separated fibers facing all directions, which improve the distribution of the liquids absorbed along the entirety of the absorbent material of said second layer, optimizing the absorption capacity of the hygiene product and preventing the user from feeling a sensation of wetness.

This protection incorporates in the absorbent layer and/or in the cotton non-woven third layer, which is intended to be in contact with the skin of the user, a plurality of microcapsules containing active ingredients for treating the skin, said ingredients being encapsulated in an outer cover of biocompatible material that degrades during the use of the hygiene product and releases the active ingredients during the use of the hygiene product.

The biocompatible material of the outer cover of the microcapsules can degrade, for example, when it comes into contact with the epidermis by means of the action of the enzymes and the natural flora of the skin, due to the acidity, humidity, due to friction, temperature or any other factors, gradually releasing the active products contained therein, which are transferred to the different layers of the skin effecting the localized treatment thereof without requiring the user to apply the product.

The increased amount of time in which the cotton non-woven layer is in contact with the body of the user improves the transference process of the active products from the microcapsules to the skin, and therefore the local treatment thereof.

These microcapsules have a high affinity with the skin in order to establish between them a chemical attraction that improves the contact thereof with each other.

The active products contained in the microcapsules can be of a different nature, for example medical products or cosmetic products, with hydrating, fungicide, bactericide, cauterizing properties or any other, depending on the treatment sought and the ailment experienced in the area where the hygiene product is applied.

The cotton non-woven layer can be hydrophilic, that is, with the capacity of retaining liquids and boosting the absorbent characteristics of the product; or hydrophobic, that is, with the capacity of avoiding humidity and boosting the characteristics of providing a dry sensation.

It should also be mentioned that in the case when the microcapsules are located in the absorbent layer, the separated fibers also help to disperse the active principle of the microcapsules along the entirety of said absorbent layer, expanding the application surface of the active product on the skin of the user.

These and other characteristics of the invention, which are detailed in the claims, will be more easily understood thanks to the attached example embodiment.

DESCRIPTION OF THE FIGURES

To complement the description being made, and to make it easier to understand the characteristics of the invention, this descriptive report is accompanied by a set of drawings in which, for illustrative purposes only and without limitation, the following has been represented.

PREFERRED EMBODIMENT OF THE INVENTION

Figure 1:
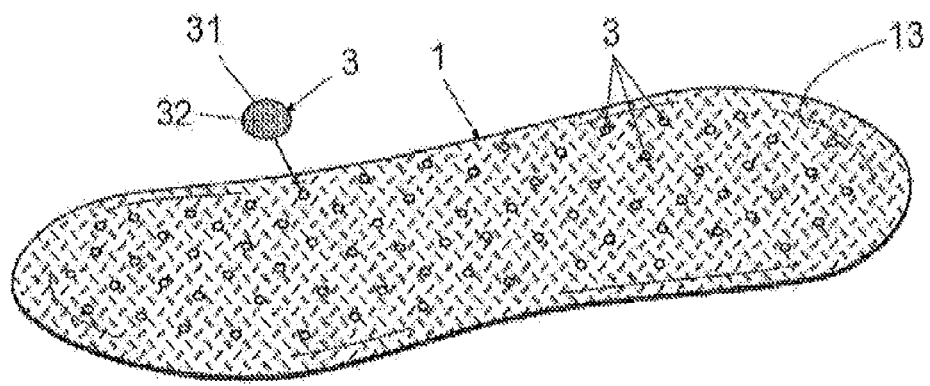
FIG. 1 shows a schematic upper perspective view of an example embodiment of the disposable hygiene product for personal use according to the invention, which is represented in this case by a sanitary tower, and a representation in expanded detail of one of the microcapsules.
Figure 2:
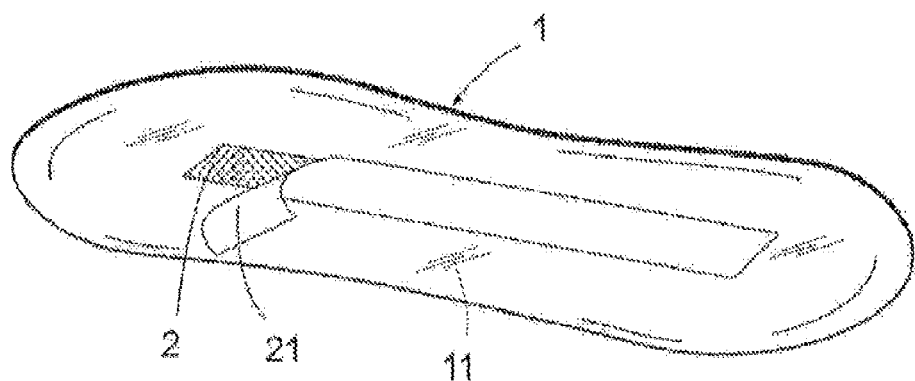
FIG. 2 shows a schematic lower perspective view of the disposable hygiene product for personal use in the previous figure, with the protective layer of the adhesive partially removed.
Figure 3:
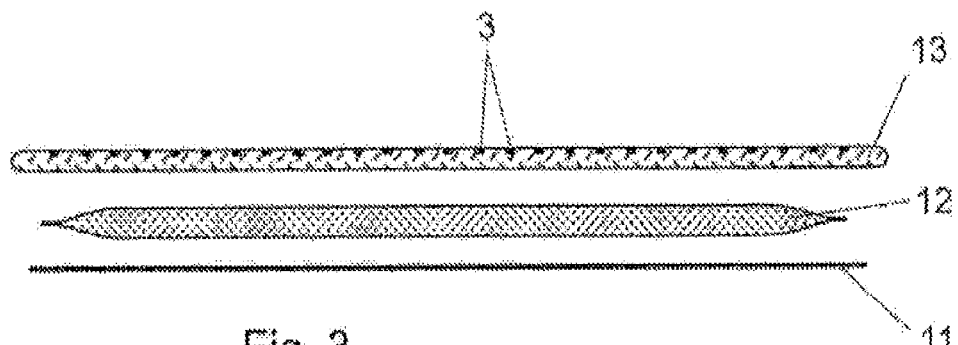
FIG. 3 shows an exploded cross-sectional view of the three layers of the sanitary towel of the previous figures, displaying a vertical plane cross-section.

The hygiene product for personal use is represented in the attached figures by means, for example, of a sanitary towel (1) comprising an impermeable breathable first outer layer (11), an intermediate second layer (12) of an absorbent material, and a third outer layer (13) made of 100% cotton non-woven fabric intended to be in contact with the skin of the user; with said layers joined together forming an extra-flat hygiene product.

The first outer layer (11) is impermeable and breathable, so that, in addition to preventing the liquids absorbed by the hygiene product (1) from coming out and staining the clothes of the user, it can also oxygenate the area covered by the hygiene product (1).

This impermeable first outer layer (11) comprises on the outer side thereof an adhesive (2), initially covered by a protective layer (21) that is disposed upon being used, in order to secure the hygiene product (1) to a garment of the user.

The absorbent second layer (12) comprises a hydrophilic cotton core formed by separated fibers facing or oriented in all directions in order to improve the distribution or dispersion of the liquids absorbed by the surface of said second layer, optimizing the absorption capacity of the hygiene product.

In this example embodiment, the hygiene product (1) incorporates in the cotton non-woven third layer (13) a series of biocompatible microcapsules (3) with an outer cover (31) containing active ingredients (32) that are cosmetic, medicinal or of any other kind.

The outer cover (31) is formed by biocompatible substances, and with a composition similar to the skin, for example based on proteins and lipids. This outer cover (31) gradually degrades during the use of the hygiene product and releases the active ingredients (32) contained in the microcapsules (3), transferring them to the skin of the user.

As Mentioned Above, the Cotton Non-Woven Third Layer (13) can be Hydrophilic or Hydrophobic.

The microcapsules (3) can also be arranged optionally or additionally over the second absorbent layer (12); in this case the separate fibers of the second absorbent layer help to disperse the active product (32) of the microcapsules (3) over said absorbent second layer (12).

Having described sufficiently the nature of the invention, and the examples of a preferred embodiment, it can be stated for the relevant effects that the materials, shape, size and arrangement of the elements described may be modified, provided this does not mean an alteration in the essential characteristics of the invention for which the claims are set out below.

The present invention is not intended to be limited to a device which must satisfy one or more of any stated or implied objects or features of the invention and should not be limited to the preferred, exemplary, or primary embodiment(s) described herein. Modifications and substitutions by one of ordinary skill in the art are considered to be within the scope of the present invention, which is not to be limited except by the allowed claims and their legal equivalents.

The invention claimed is:

1. A hygiene product for personal use, comprising at least an impermeable and breathable first layer, a liquid-absorbing second layer and a third layer of a cotton non-woven fabric configured for being in contact with the skin of the user, wherein
   the liquid-absorbing second layer comprises a hydrophilic cotton core formed by separated fibers facing all directions, and
   a plurality of microcapsules is incorporated in the liquid-absorbing second layer and the third layer of a cotton non-woven fabric, and
   said microcapsules contain active ingredients for treating the skin, said ingredients being encapsulated in an outer cover of biocompatible material that degrades during the use of the hygiene product and releases the active ingredients during the use of the hygiene product.

2. The hygiene product according to claim 1, wherein the third layer of a cotton non-woven fabric is hydrophilic.

3. The hygiene product according to claim 1, wherein the third layer of a cotton non-woven fabric is hydrophobic.

4. The hygiene product according to claim 1, wherein the impermeable and breathable first layer comprises on the outer side thereof an adhesive far securing the product to a garment of the user, which is covered initially by a disposable protective sheet.

5. The hygiene product of claim 1, wherein said hygiene product is selected from the group of hygiene products consisting of a sanitary towel, a dressing, a tampon, an absorbent nappy and a nursing pad.

* * * * *